United States Patent [19]
Horrobin et al.

[11] Patent Number: 5,859,055
[45] Date of Patent: *Jan. 12, 1999

[54] METHOD OF PREVENTING OCCLUSION OF ARTERIES

[75] Inventors: David F. Horrobin; John C. M. Stewart, both of Guildford, England

[73] Assignee: Scotia Holdings PLC, United Kingdom

[*] Notice: The term of this patent shall not extend beyond the expiration date of Pat. No. 5,378,732.

[21] Appl. No.: 557,545

[22] Filed: Nov. 14, 1995

Related U.S. Application Data

[60] Continuation of Ser. No. 306,935, Sep. 16, 1994, abandoned, which is a division of Ser. No. 981,116, Nov. 25, 1992, Pat. No. 5,378,732.

[30] Foreign Application Priority Data

Dec. 2, 1991 [GB] United Kingdom ................. 91256024

[51] Int. Cl.$^6$ ........................... A61K 31/22; A61K 31/20
[52] U.S. Cl. ........................... 514/549; 514/560; 514/824
[58] Field of Search ................... 514/549, 560, 514/824

[56] References Cited

U.S. PATENT DOCUMENTS

| | | | |
|---|---|---|---|
| 4,526,902 | 7/1985 | Rubin | 514/560 |
| 4,780,456 | 10/1988 | Pistolesi | 514/560 |
| 4,920,098 | 4/1990 | Cotter et al. | 514/2 |
| 5,059,622 | 10/1991 | Sears | 514/560 |

OTHER PUBLICATIONS

Database WPIL, Week 8534, Derwent Publications Ltd., London, GB; AN 85–207768 & JP–A–60 132 916 (Nisshin Oil Mills KK), Abstract (1985).

Lechleitner et al., Wiener Medizinische Wochenschrift, vol. 140, No. 10, Jun. 1990 pp. 277–278, "Medikamentöse Prophylaxe nach koronarer Bypassoperation order PTCA".

Aoki et al., Prostaglandins Leukotriens and Essential Fatty Acids, vol. 37, No. 2, pp. 89–95, "Acute Effects of unsaturated fatty etc." (1989).

European Search Report of European Application No. 92310807 (May 12, 1993).

Passwater, Richard A., "Evening Primrose Oil" (1981) pp. 1–11.

Cox et al *Canadian Journal of Cardiology*, vol. 4. No 4 May 1988:201–210 "Review of antiplatelet drug use in preventing restenosis following percutaneous transluminal coronary angioplasty".

Leaf et al *Circulation* vol. 90, No. 5 Nov. 1994 "Do Fish Oils Prevent Restenosis After Coronary Angioplasty?".

*Primary Examiner*—Raymond Henley, III
*Attorney, Agent, or Firm*—Nixon & Vanderhye

[57] ABSTRACT

Gamma-linolenic acid and/or dihomo-gamma-linolenic acid is used in the preparation of a medicament for inhibiting reocclusion of an artery from which an occlusion or other blockage has been removed, or for preventing occlusion of peripheral or coronary arteries. The medicament may also comprise eicosapentaenoic acid.

12 Claims, No Drawings

METHOD OF PREVENTING OCCLUSION OF ARTERIES

This is a continuation of Ser. No. 08/306,935, filed 16 Sep. 1994, now abandoned, which is a Rule 60 Diviwion of application Ser. No. 07/981,116, filed 25 Nov. 1992, now U.S. Pat. No. 5,578,732.

The present invention relates to a method of inhibiting occlusion of arteries, and to the use of GLA and/or DGLA for the preparation of a medicament for use in said method.

Arteries frequently become partially or totally occluded by atherosclerosis. Over the past twenty years, many methods have been developed aimed at clearing obstructions and allowing the free flow of blood. Such methods have included direct surgical techniques, the introduction of balloons, or other devices, attached to catheters which, when expanded at an appropriate site, partially or completely clear the blockage, and the use of lasers to blast away the occlusion.

Unfortunately, however, the artery does not always remain open. Sometimes it becomes blocked again very quickly because of a thrombosis. More frequently it closes after weeks, months or even years as a result of the redevelopment of the atherosclerosis. These closures are known as reocclusions. Depending on various factors, such as the technique used, may arteries are found to reocclude. Typically, 20–40% of opened arteries close again.

Thus, it would be highly advantageous if initial occlusion could be prevented. The benefits to patients and the saving of costs would be considerable.

The invention provides a method for preventing occlusion of peripheral or coronary arteries by administering a composition comprising an effective, non-toxic amount of γ-linolenic acid or dihomo-γ-linolenic acid.

The γ-linolenic acid or dihomo-γ-linolenic acid may be administered in the form of any appropriate derivative such as the free acid, the potassium, lithium or other alkali metal salt, a salt of another metal, eg. zinc, calcium or magnesium, the mono-, di- or triglyceride, ethyl or any other appropriate esters, phospholipids, amides or any other derivative which will lead to elevation of γ-linolenic acid or dihomo-γ-linolenic acid and/or its metabolites in the body.

In a second aspect of the invention there is provided use of γ-linolenic acid or dihomo-γ-linolenic acid for the manufacture of a medicament for the inhibition of reocclusion of an artery from which an occlusion or other blockage has been removed.

The invention also embraces the use of γ-linolenic acid or dihomo-γ-linolenic acid for the manufacture of a medicament for preventing occlusion of peripheral or coronary arteries.

Administration of capsules containing γ-linolenic acid in combination with eicosapentaenoic acid, over a period of up to 1 year, to patients who have had an occlusion of the femoral artery removed by balloon angioplasty, has been found to result in a significant reduction of the reocclusion rate. There is every reason to believe that such reductions in the reocclusion rate will also be observed on administration of compositions of the invention following coronary angioplasty, as well as methods of reopening blood vessels other than angioplasty. Since GLA, with EPA is particulary effective and used to prevent reocclusion, it is also likely to be able to prevent occlusion in the first place and such prevention of occlusion of peripheral or coronary arteries is within the scope of this invention.

In the compositions of the present invention, it is preferred that γ-linolenic acid or dihomo-γ-linolenic acid is administered in a dose of from 1 mg to 10 g/day, preferably 100 mg to 4 g/day, particularly 500 mg to 2 g/day. Such compositions may optionally further contain eicosapentaenoic acid, as stated above, the additional dose of eicosapentaenoic acid being from 1 mg to 10 g/day, preferably 100 mg to 4 g/day, particularly 500 mg to 2 g/day. In particularly preferred compositions, the amount of eicosapentaenoic acid in the pharmaceutical compositions is relatively smaller compared to the amount of γ-linolenic acid or dihomo-γ-linolenic acid. The ratio of γ-linolenic acid:eicosapentaenoic acid is typically from 20:1 to 3:1.

The γ-linolenic acid or dihomo-γ-linolenic acid, either singly or in combination, further optionally in combination with eicosapentaenoic acid, may be administered orally in any appropriate dosage form, such as soft or hard gelatin capsules, which may or may not be enteric-coated, tablets, whips, liquids, internal formulations or any other appropriate formulation known to those skilled in the art. The medicaments may also be administered topically, parenterally by injection (intravenous, intradermal or subcutaneous), infusion or any other appropriate route, rectally or vaginally.

Soft or hard gel gelatin capsules, enteric coated or not, for example, may contain 100, 200, 300 or 600 mg of γ-linolenic acid in any appropriate form, optionally with an appropriate amount of eicosapentaenoic acid in any appropriate form.

Further examples include an emulsion for intravenous administration which may contain 100 mg of γ-linolenic acid/ml optionally with 5–30 mg of eicosapentaenoic acid/ml, a cream for topical administration which may contain 1–20% of triglyceride γ-linolenic acid, while a suppository for rectal administration or a pessary for vaginal administration may contain 1 g of γ-linolenic acid in an appropriate formulation.

The invention is further illustrated by the following, non-limiting example.

EXAMPLE

Patients with occlusion of the femoral artery were entered into the study. The occlusion was treated by balloon angioplasty. One week prior to the angioplasty patients commenced treatment with either 6 capsules/day of placebo or 6 capsules/day of 270 mg of γ-linolenic acid and 45 mg of eicosapentaenoic acid. Treatment with active drug or placebo then continued for one year after angioplasty. Blood flow in the femoral artery was monitored before angioplasty, 1–2 days after angioplasty and at 6 months and 12 months using Doppler flowmetry. If symptoms suggesting reocclusion developed at any time during the study, Doppler flowmetry was performed and if occlusion was suspected this was confirmed by performing an angiogram.

60 patients entered the study and 46 have completed one year. 30 patients received active and 30 placebo treatment.

Of the 46 patients who have completed one years treatment at the time of writing, 23 were assigned to active treatment, and 23 to placebo.

In the patients in the active group, the arteries of 19 patients have remained open, while 4 have reoccluded. In the placebo group, the arteries of 12 patients have remained open, while 11 have reoccluded.

This is a significant reduction of the reocculsion rate, showing that γ-linolenic acid in combination with eicosapentaenoic acid is highly effective in preventing reocclusion after femoral angioplasty.

We claim:

1. A method of reducing the occurrence of thrombotic and atherosclerotic occlusion of peripheral or coronary arteries by administering to a person in need of same and at risk of occlusion and of needing an angioplastic procedure, a composition comprising an effective, non-toxic amount of γ-linolenic acid or dihomo-γ-linolenic acid or both.

2. A method according to claim 1, wherein the γ-linolenic acid or dihomo-γ-linolenic acid is administered in a dose range of from 1 mg to 10 g/day.

3. A method according to claim 2, wherein the γ-linolenic acid or dihomo-γ-linolenic acid is administered in a dose range of from 100 mg to 4 g/day.

4. A method according to claim 3, wherein the γ-linolenic acid or dihomo-γ-linolenic acid is administered in a dose range of from 500 mg to 2 g/day.

5. A method according to claim 1, wherein the composition further comprises eicosapentaenoic acid.

6. A method according to claim 5, wherein the eicosapentaenoic acid is administered in an amount of from 1 mg to 10 g/day.

7. A method according to claim 6, wherein the eicosapentaenoic acid is administered in an amount of from 100 mg to 4 g/day.

8. A method according to claim 7, wherein the eicosapentaenoic acid is administered in an amount of from 500 mg to 2 g/day.

9. A method according to claim 5, wherein the composition comprises a relatively smaller amount of eicosapentaenoic acid than of γ-linolenic acid or dihomo-γ-linolenic acid.

10. A method according to claim 9, wherein the composition comprises a ratio of γ-linolenic acid or dihomo-γ-linolenic acid to eicosapentaenoic acid of from 20:1 to 3:1.

11. A method of reducing the occurrence of thrombotic and atherosclerotic occlusion of peripheral or coronary arteries by administering to a person in preparation for an angioplastic procedure a composition comprising an effective, non-toxic amount of γ-linolenic acid or dihomo-γ-linolenic acid or both.

12. A method of reducing the occurrence of thrombotic and atherosclerotic occlusion of peripheral or coronary arteries by administering to a person subsequent to an angioplastic procedure a composition comprising an effective, non-toxic amount of γ-linolenic acid or dihomo-γ-linolenic acid or both.

* * * * *